(12) United States Patent
Turco et al.

(10) Patent No.: US 12,258,387 B2
(45) Date of Patent: Mar. 25, 2025

(54) ANTI-BAG3 ANTIBODIES AS THERAPEUTIC REAGENT IN CARDIOVASCULAR DISEASE

(71) Applicant: FIBROSYS S.R.L., Baronissi (IT)

(72) Inventors: Maria Caterina Turco, Avellino (IT); Liberato Marzullo, Scalea (IT); Alessandra Rosati, Baronissi (IT); Margot De Marco, Salerno (IT); Anna Basile, Bracigliano (IT)

(73) Assignee: FIBROSYS S.R.L., Baronissi (IT)

( * ) Notice: Subject to any disclaimer, the term of this patent is extended or adjusted under 35 U.S.C. 154(b) by 0 days.

(21) Appl. No.: 17/703,747

(22) Filed: Mar. 24, 2022

(65) Prior Publication Data

US 2022/0213182 A1 Jul. 7, 2022

Related U.S. Application Data

(62) Division of application No. 17/040,468, filed as application No. PCT/EP2018/070259 on Jul. 26, 2018, now abandoned.

(30) Foreign Application Priority Data

Jul. 28, 2017 (IT) .......................... 102017000087307
Oct. 10, 2017 (IT) .......................... 102017000113648

(51) Int. Cl.
| | | |
|---|---|---|
| A61K 39/395 | (2006.01) | |
| A61P 9/04 | (2006.01) | |
| A61P 9/10 | (2006.01) | |
| C07K 16/18 | (2006.01) | |
| A61K 39/00 | (2006.01) | |

(52) U.S. Cl.
CPC .......... *C07K 16/18* (2013.01); *A61K 39/3955* (2013.01); *A61P 9/04* (2018.01); *A61P 9/10* (2018.01); *A61K 2039/505* (2013.01); *C07K 2317/20* (2013.01); *C07K 2317/24* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/626* (2013.01)

(58) Field of Classification Search
CPC .......... A61K 39/3955; A61P 9/04; A61P 9/10
See application file for complete search history.

(56) References Cited

U.S. PATENT DOCUMENTS

| | | |
|---|---|---|
| 10,889,644 B2 | 1/2021 | Turco et al. |
| 2016/0168255 A1* | 6/2016 | Turco .................. A61P 9/00 424/143.1 |

FOREIGN PATENT DOCUMENTS

| | | |
|---|---|---|
| EP | 0239400 A2 | 9/1987 |
| EP | 0451216 B2 | 6/2012 |
| WO | WO-03055908 A2 * | 7/2003 ......... C07K 14/4747 |
| WO | 2011067377 A1 | 6/2011 |
| WO | 2015117010 A2 | 8/2015 |
| WO | 2017031182 A2 | 2/2017 |
| WO | 2017076878 A1 | 5/2017 |

OTHER PUBLICATIONS

Benjamini et al., 1991. Immunology: A Short Course, 2nd edition, p. 40 only.*
Ferrara et al (2015. mAbs. 7(1): 32-41.*
International Search Report of PCT/EP2018/070259, mailed Jul. 9, 2018, 5 pages., Jul. 9, 2018.
Ammirante, Massimo, et al., "IKKγ protein is a target of BAG3 regulatory activity in human tumor growth", www.pnas.org/cgi/doi/10.1073/pnas.0907696107., 2010, pp. 1-6.
Behl, Christian, "Breaking BAG: The Co-Chaperone BAG3 in Health and Disease", Trends in Pharmacological Sciences, Aug. 2016, vol. 37, No. 8, 2016, pp. 672-688.
Belkaya, Serkan, et al., "Autosomal Recessive Cardiomyopathy Presenting as Acute Myocarditis", Journal of the American College of Cardiology, vol. 69, No. 13, 2017, 2017, pp. 1653-1665.
Carriizzo, Albino, et al., "The prosurvival protein BAG3: a new participant in vascular homeostasis", Cell Death and Disease (2016) 7, e2431; doi: 10.1038/cddis.2016.321, Official journal of the Cell Death Differentiation Association, 6 pages., 2016.
Ceran, Ceyhan, et al., "Novel anti-HER2 monoclonal antibodies: synergy and antagonism with tumor necrosis factor-a", BioMed Central 2012, 2012, pp. 1-16.
De Marco, Margot, et al., "BAG3 Protein in Advanced-Stage Heart Failure", JACC: Heart Failure vol. 2, No. 6, 2014, pp. 673-675.
De Marco, M., et al., "Detection of soluble BAG3 and anti-BAG3 antibodies in patients with chronic heart failure", Cell Death and Disease (2013) 4, e495; doi:10.1038/cddis.2013.8 & 2013 Macmillan Publishers Limited All rights reserved 2041-4889/13, 2 pages., 2013.
Festa, Michelina, et al., "BAG3 Protein Is Overexpressed in Human Glioblastoma and is a Potential Target for Therapy", The American Journal of Pathology, vol. 178, No. 6, Jun. 2011, 2011, pp. 2504-2512.
Gourdie, Robert G., et al., "Novel therapeutic strategies targeting fibroblasts and fibrosis in heart disease", Nature Reviews | Drug Discovery; vol. 15, Sep. 2016, 2016, pp. 620-638.
Keah, Hooi Hong, et al., "Direct synthesis and characterisation of multi-dendritic peptides for use as immunogens", Center for Biopress Technology, Dept. of Biochemistry and Molecular Biology; Journal of Peptide Research, 1997, pp. 2-8.
Kettleborough, Catherine A., et al., "Humanization of a mouse monoclonal antibody by CDR-grafting: the Importance of framework residues on loop confirmation", Protein Engineering, vol. 4, No. 7, 1991, pp. 773-783.
Ota, Seisuke, et al., "Cellular Processing of a Multibranched Lysine Core with Tumor Antigen Peptides and Presentation of Peptide Epitopes Recognized by Cytotoxic T Lymphocytes on Antigen-presenting Cells", Cancer Research 62, Mar. 1, 2002, 2002, pp. 1471-1476.

(Continued)

Primary Examiner — Zachary C Howard
(74) Attorney, Agent, or Firm — Perkins Coie LLP; Viola T. Kung

(57) ABSTRACT

The present invention relates to the use of anti-BAG3 antibodies and its pharmaceutical formulation in the treatment of cardiovascular diseases.

8 Claims, 1 Drawing Sheet

Specification includes a Sequence Listing.

(56) References Cited

OTHER PUBLICATIONS

Polizzotti, Brian D., et al., "A cryoinjury model in neonatal mice for cardiac translational and regeneration research", Author manuscript, Mar. 2016, 2016, pp. 542-552.

Rosati, Alessandra, et al., "BAG3 promotes pancreatic ductal adenocarcinoma growth by activating stromal macrophages", Nature Communication; DOI: 10.1038/ncomms9695, 2015, pp. 1-11.

Rosati, A., et al., "BAG3: a multifaceted protein that regulates major cell pathways", Citation: Cell Death and Disease (2011) 2, eK; doi:10.1038/cddis.2011.24, 2011, pp. 1-6.

Rosati, Alessandra, et al., "Expression of the Antiapoptotic Protein BAG3 is a Feature of Pancreatic Adenocarcinoma and Its Overexpression is Associated With Poorer Survival", Short Communications, The American Journal of Pathology, vol. 181, No. 5, Nov. 2012, 2012, pp. 1524-1529.

Ruparelia, Neil, et al., "Inflammatory processes in cardiovascular disease: a route to targeted therapies", Nature Reviews | Cardiology, doi: 10.1038/nrcardio.2016.185, Dec. 2016, 2016, pp. 1-12.

Tam, James P., "Synthetic peptide vaccine design: Synthesis and properties of a high-density multiple antigenic peptide sytsem", Proc. Natl. Acad. Sci. USA, vol. 85, Aug. 1988, 1988, pp. 5409-5413.

Tassone, P., et al., "CD35 is rapidly and transiently upregulated on phytohemagglutinin (PHA)-stimulated peripheral blood lymphocytes. Analysis by a new monoclonal antibody (UN7)", CD35 upregulation on PHA-Stimulated PBL, Tissue Antigens, 1998, pp. 672-675.

Travers, Joshua G., et al., "Cardiac Fibrosis—The Fibroblast Awakens", Heart Institute, Division of Molecular Cardiovascular Biology, Cincinnati Children's Hospital Medical Center, OH., 2016, pp. 1021-1040.

\* cited by examiner

A
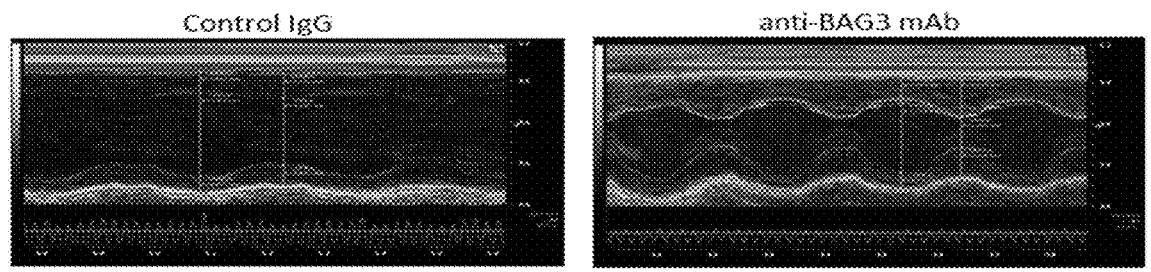
B
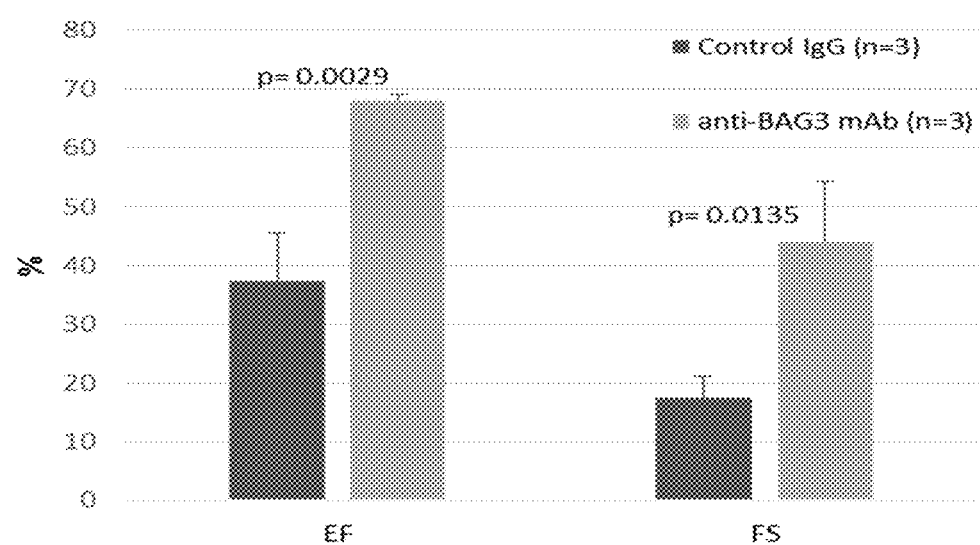
C
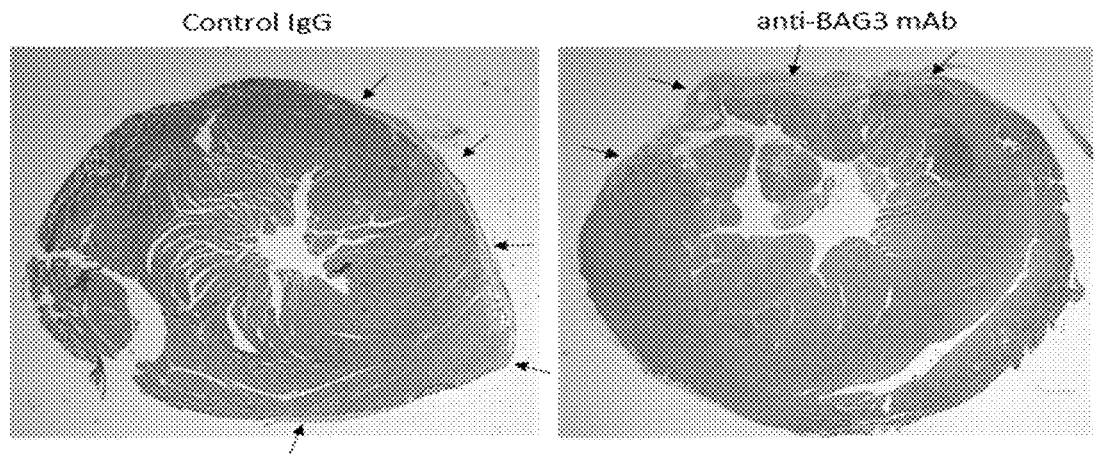

ANTI-BAG3 ANTIBODIES AS THERAPEUTIC REAGENT IN CARDIOVASCULAR DISEASE

This application is a divisional of U.S. application Ser. No. 17/040,468, filed Sep. 22, 2020; which is a 371 application of PCT/EP2018/070259, filed Jul. 26, 2018; which claims the priority of Italian applications 102017000113648, filed Oct. 10, 2017, and 102017000087307, filed Jul. 28, 2017. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Mar. 18, 2022, and a size of 36.5 kilobytes. The Sequence Listing filed via EFS-Web is part of the specification and is hereby incorporated in its entirety by reference herein.

FIELD OF THE INVENTION

The present invention relates to the use of anti-BAG3 antibodies and its pharmaceutical formulation in the treatment of cardiovascular diseases.

BACKGROUND OF THE INVENTION

BAG3 protein is a 74 kDa cytoplasmic protein which belongs to the family of co-chaperons that interact with the ATPase domain of the protein HSP70 (Heat Shock Protein) through the structural domain known as the BAG domain (amino acids 110-124). Furthermore, BAG3 protein contains a WW domain (Trp-Trp), a proline-rich region (PXXP), and two conserved motifs IPV (Ile-Pro-Val), which can mediate binding to other proteins. Thanks to the nature of BAG3 protein as an adapter, attributable to the presence of many functional domains, such protein can therefore interact with different proteins.

In humans, bag3 gene expression is constitutive for a few kinds of normal cells, including myocytes, while mutations thereof are associated with diseases of the skeletal and cardiac muscles. Furthermore, BAG3 protein is expressed in many types of primary tumors or tumor cell lines (lymphoid or myeloid leukemias, neuroblastoma, pancreatic cancer, thyroid cancer, breast cancer and prostate cancer, melanoma, osteosarcoma, glioblastoma and tumors of the kidney, colon, ovary, etc.) (Rosati A. et al Cell Death Dis. 2011 Apr. 7; 2:e141).

In normal cell types, such as leukocytes, epithelial cells and glial cells and cells of the retina, bag3 gene expression can be induced by stressors, such as oxidants, high temperatures, lack of serum, heavy metals, HIV-1 infections, etc. These findings indicate that bag3 gene expression regulation is an important component in the cellular response to stress and is correlated with the presence of elements that respond to the transcription factor HSF1 (Heat Shock Transcription Factor), which is activated in various forms of cellular stress in bag3 gene promoter. Moreover, due to the presence of many protein-protein interaction domains in the structure thereof, BAG3 protein influences cell survival in different types of cells, interacting with different molecular partners (Rosati A. et al Cell Death Dis. 2011 Apr. 7; 2:e141). The first mechanism reported in relation to BAG3 anti-apoptotic activity was identified in osteosarcoma and melanoma cells, where it was observed that BAG3 protein modulates the activation of transcription factor NF-κB and cell survival (Ammirante M. et al. Proc Natl Acad Sci USA. 2010; 107(16):7497-502.). A different molecular mechanism has been described in glioblastoma cells, where BAG3 protein cooperates in a positive way with HSP70 protein to maintain BAX protein in the cytosol and prevent the translocation thereof into the mitochondria (Festa M. et al. Am J Pathol. 2011; 178(6):2504-12). Finally, in some tumors, BAG3 has been shown to regulate proteins that modulate cell adhesion.

The presence of cytoplasmic BAG3 protein has also been described in many different cellular systems and has been associated, not only with various tumors, but also in pathologies in general related to cell survival.

Furthermore, patent application n. WO2011/067377 describes extracellular BAG3 protein, secreted by some cell types, as a biochemical marker in serum, which is highly specific for the diagnosis of certain pathological conditions, such as cardiac pathologies and pancreatic tumor.

It has recently been reported that BAG3 protein is expressed in 346/346 patients with pancreatic ductal adenocarcinoma (PDAC) and is released by the cells of the pancreatic tumor, as a soluble protein, but such protein is not expressed in either the surrounding non-neoplastic tissues or in a normal pancreas; likewise, it has been reported that the levels of BAG3 expression are related to patient survival. The results of the study demonstrate that the use of specific siRNA molecules for BAG3 mRNA can silence bag3 gene expression and induce cell death, confirming that BAG3 protein is an important survival factor for pancreatic tumor cells and that the down-regulation thereof, when combined with gemcitabine, may contribute to the eradication of the tumor cells (Rosati A. et al. Am J Pathol. 2012 November; 181(5):1524-9).

Moreover, in a recent paper (Rosati A. et al. Nat Commun. 2015 Nov. 2; 6:8695), we have reported that PDAC-released BAG3 binds macrophages inducing their activation and the secretion of PDAC supporting factors. We have also identified IFITM-2 as a BAG3 receptor and showed that it signals through PI3K and the p38 MAPK pathways. Finally, we have showed that the use of a mouse monoclonal anti-BAG3 antibody results in reduced tumor growth and prevents metastasis formation in three different mouse models. We have therefore identified a paracrine loop involved in PDAC growth and metastatic spreading, and showed that an anti-BAG3 antibody has therapeutic potential (Rosati A. et al. Nat Commun. 2015 Nov. 2; 6:8695).

Indeed, we showed that an anti-BAG3 antibody blocked BAG3 activity on macrophages. In vivo, we showed the ability of this antibody to block tumor growth in different animal models, including a model of patient-derived xenograft and a syngeneic model. This last model is of great importance since mice have an intact immune system.

Intracellular BAG3 protein is known to maintain cardiomyocyte homeostasis and myofibrillar integrity during mechanical, proteotoxic and other types of stress; such property is related to BAG3 anti-apoptotic activity, participation in macroautophagy, and structural role in myofibrils. Therefore, BAG3 defects can result in impairing cardiomyocyte survival or contractility and producing arrhythmias, dilated cardiomyopathy, or Takotsubo cardiomyopathy (C. Behl. Breaking BAG: The Co-Chaperone BAG3 in Health and Disease. Trends Pharmacol. Sci. 2016; 37:672-688). Carizzo et al. (Cell Death and Disease, 2016, 7; e2431) discloses that soluble BAG3, released by stressed cardiomyocytes, has a role in regulating blood pressure levels and in modulating the vascular tone and investigate the possible hemodynamic effect of BAG3.

Furthermore WO2015/117010A3 reports the use of composition comprising molecules that increase the intracellular expression of BAG3 and its use in the treatment of heart failure, providing evidences that the BAG3 levels are decreased in the failing heart. However, all the information reported above relates to the intracellular BAG3 protein and to its effect in maintaining the normal functional heart.

We have now discovered a new and different aspect of BAG3 extracellular (soluble) activity that can contribute to its role in inflammatory diseases, in particular in heart diseases, such as AVM (Acute Viral myocarditis) (S. Belkaya, A. R. Kontorovich, M. Byun, et al. J Am Coll Cardiol. 2017; 69:1653-1665). Indeed, in different systems, we demonstrated that BAG3 is secreted by stressed cardiomyocytes (M. De Marco, R. D'Auria, A. Rosati, et al. BAG3 protein in advanced-stage heart failure. JACC Heart Fail. 2014; 2:673-675) and that it binds to specific receptors on macrophages inducing their activation (Rosati A. et al. Nat Commun. 2015 Nov. 2; 6:8695).

Therefore, if some BAG3 variation(s) facilitate its release, this might expectedly result in macrophages-driven cardiac inflammation. Furthermore, since activated macrophages produce fibrogenic cytokines, it might be predicted that BAG3 release, by activating macrophages, can stimulate the fibrotic process, resulting in reducing the Left Ventricular Ejection Fraction (LVEF), that is a measure of the efficiency of pumping into the systemic circulation and serves as a general measure of a person's cardiac function. In particular, a low ejection fraction is always associated with an heart disease.

In this view, BAG3 neutralization should be able to improve LVEF and therefore to preserve normal cardiac functions. This prediction appears supported by data from our laboratory.

It has also been reported that fibrotic and inflammatory processes appear to be some of the integral components that causes most of the cardiac pathologies, such as angina pectoris, pre-infarction angina, myocardial infarction, heart failure, ischemia, acute coronary disease, acute heart failure, chronic heart failure and iatrogenic heart disease (Ruparella N. et al., Nature Reviews, Online 1, 2016, pp. 1-12; Gourdie R G et al., Nature, Vol. 15, 2016, pp. 620-638). Furthermore, nearly all etiologies of heart disease involve pathological myocardial remodeling characterized by excessive deposition of extracellular matrix (ECM) proteins by cardiac fibroblasts (CFs), which reduces tissue compliance and accelerates the progression to heart failure (Joshua G. et al., Circ. Res. 2016 Mar. 18; 118(6):1021-40.)

Conventional treatments for cardiovascular diseases inhibiting or reversing fibrosis and its adverse consequences, such as ACE-inhibitors, aldosterone antagonism statins and β-blockers, pose numerous drawbacks linked to side effects and are not, at present, definitive means of treating such pathologies.

There is therefore an evident need for a new and improved therapeutic treatment that the target cardiac diseases processes linked to fibroblast function, which has the advantage of being highly specific and having few or no side effects, as compared with the conventional, commonly known therapies used for the treatment of cardiovascular diseases, such as angina pectoris, pre-infarction angina, myocardial infarction, heart failure, ischemia, acute coronary disease, acute heart failure, chronic heart failure and iatrogenic heart disease, that are caused by an inflammatory and fibrotic process.

Definitions

Unless otherwise defined, all terms of art, notations and other scientific terminology used herein are intended to have the meanings commonly understood by those persons skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "soluble BAG3 protein" is understood as extracellular BAG3 protein, i.e. the protein secreted externally to the cell.

The term "pharmaceutically acceptable excipient" herein refers to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition 2009, herein incorporated by reference.

The term "simultaneous, separate or sequential administration" herein refers to administration of the first and second compounds at the same time or in such a manner that the two compounds act in the patient's body at the same time or administration of one compound after the other compound in such a manner to provide a therapeutic effect. In some embodiments the compounds are taken with a meal. In other embodiments, the compounds are taken after a meal, such as 30 minutes or 60 minutes after a meal. In some embodiments, one compound is administered to a patient for a time period followed by administration of the other compound.

The terms "approximately" and "about" herein refer to the range of the experimental error, which may occur in a measurement.

The terms "comprising", "having", "including" and "containing" are to be construed open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as semi-closed terms, meaning that no other ingredients which materially affects the basic and novel characteristics of the invention are included (optional excipients may thus included).

The terms "consists of", "consisting of" are to be construed as closed terms.

The term "antibody" as used herein includes "fragments" or "derivatives", which have at least one antigen binding site of the antibody and/or show the same biological activity.

An antibody preferably comprises at least one heavy immunoglobulin chain and at least one light immunoglobulin chain. An immunoglobulin chain comprises a variable domain and optionally a constant domain. A variable domain may comprise complementarity determining regions (CDRs), e.g. a CDR1, CDR2 and/or CDR3 region, and framework regions.

The term "humanized antibody" refers to an antibody of human origin, whose hypervariable region has been replaced by the homologous region of non-human monoclonal antibodies.

The term "chimeric antibody" refers to an antibody containing portions derived from different antibodies.

The term "recombinant antibody" refers to an antibody obtained using recombinant DNA methods.

The term "scFv fragment" (single chain variable fragment) refers to immunoglobulin fragments only capable of binding with the antigen concerned. ScFv fragments can also be synthesised into dimers (diabodies), trimers (triabodies) and tetramers (tetrabodies) using peptide linkers.

The terms "Fab fragment" (antigen-binding fragment) and "Fab2 fragment" refer to immunoglobulin fragments consisting of a light chain linked to the Fc fragment of the adjacent heavy chain, and such fragments are monovalent antibodies. When the Fab portions are in pairs, the fragment is called Fab2.

The term "hybridoma" refers to a cell producing monoclonal antibodies.

The term "monospecific antibodies" refers to antibodies that all have affinity for the same antigen.

The term "multispecific antibodies" refers to antibodies that have affinity for several antigens.

The term "bispecific antibody" refers to an antibody that has affinity for two different antigens.

The term "sequence identity" between two polypeptide sequences, indicates the percentage of amino acids that are identical between the sequences.

DESCRIPTION OF THE FIGURES

FIG. 1.
A. M-mode hearts ultrasound imaging recordings in end diastole and end systole.
B. Graph depicting calculation of ejection fraction (EF) and fractional shortening (FS).
C. Masson's trichrome staining for collagen fibers.

DISCLOSURE OF THE INVENTION

Surprisingly, it has been demonstrated, for the first time, that the inhibition of soluble (i.e. extra-cellular) BAG3 protein through the use of anti-BAG3 monoclonal antibodies, impairs development of heart failure.

In particular, we found that in mice subjected to heart cryoinjury (B. D. Polizzotti, B. Ganapathy, B. J. Haubner, J. M. Penninger, B. Kühn. A cryoinjury model in neonatal mice for cardiac translational and regeneration research. Nat Protoc. 2016; 11:542-552), LVEF was reduced after five weeks, while was significantly higher in animals treated with a BAG3-neutralizing monoclonal antibody (FIG. 1). Furthermore fibrosis, measured by Masson's trichrome staining of collagen fibers, increased in mice treated with PBS, while was markedly reduced in mice that received the murine anti-BAG3 mAb under the same conditions.

The results obtained in the experimental data therefore demonstrates that reducing the level of BAG3 leads to a reduced inflammation and fibrotic process with an improvement of LVEF, that contribute to preserve the normal cardiac functions.

Anti-BAG3 antibodies therefore represent a new and improved therapeutic tool for the treatment of heart diseases.

Therefore, the treatment with any of the anti-BAG3 antibodies described in the patent application n. WO03/055908 and with any of the humanized anti-BAG3 antibodies discloses in WO2017/076878, whose content is herein entirely incorporated by reference, that is able to inhibit, specifically, the activity of soluble BAG3 protein (i.e. extra-cellular) on macrophages and fibroblasts, that are considered the target cells, proves particularly effective in the treatment of those pathologies characterised by the activation of macrophages, such as heart diseases.

In particular, the use of anti-BAG3 antibodies in this process has the surprising advantage of being more specific for the selected pathological states characterised by the over-expression and release of BAG3 protein, and also less damaging in terms of side effects.

One aim of the present invention is therefore the use of anti-BAG3 antibodies in the treatment of cardiovascular diseases.

Preferably said cardiovascular diseases are selected from angina pectoris, pre-infarction angina, myocardial infarction, heart failure, ischemia, acute coronary disease, acute heart failure, chronic heart failure and iatrogenic heart disease.

The antibodies useable in accordance with the present invention may be either monoclonal or polyclonal antibodies, and are preferably monoclonal antibodies.

Still more preferably, said monoclonal antibodies may be chosen from the following: murine antibodies, humanized antibodies, chimeric antibodies, recombinant antibodies, conjugated antibodies, scFv fragments (diabody, triabody and tetrabody), Fab fragments, and fragments F (ab') 2.

The monoclonal antibodies used in the examples were obtained by immunizing mice against four distinct BAG3 protein peptides using any method known to a person skilled in the art. Such peptides were chosen because they are BAG3 protein-specific and are not shared with any other protein, including BAG proteins.

The sequences of the four peptides are included in the BAG3 amino acid sequence (RefSeq: NP_004272; Gene ID 9531) and are selected from the following: SEQ ID NO 1 DRDPLPPGWEIKIDPQ; (includes BAG3 protein amino acids 18-33); SEQ ID NO 2: SSPKSVATEERAAPS; (includes BAG3 protein amino acids 385-399); SEQ ID NO 3: DKGKKNAGNAEDPHT; (includes BAG3 protein amino acids 533-547); SEQ ID NO 4: NPSSMTDTPGNPAAP; (includes BAG3 protein amino acids 561-575). Preferably, said antibodies may be obtained by means of the Multiple Antigene Peptide approach (MAP) (Keah H H et al., J Pept Res (1988); 51: 2. Tam J P et al; Proc Natl acad Sci USA (1988), 85: 5409. Ota S, et al., Cancer Res (2002), 62: 1471), using the following map constructs:

MAP-BAG3-1: nh2-DRDPLPPGWEIKIDPQ-MAP (which contains sequence SEQ ID NO: 1);
MAP-BAG3-2: nh2-SSPKSVATEERAAPS-MAP (which contains sequence SEQ ID NO: 2);
MAP-BAG3-3: nh2-DKGKKNAGNAEDPHT-MAP (which contains sequence SEQ ID NO: 3);
MAP-BAG3-4: nh2-NPSSMTDTPGNPAAP-MAP (which contains sequence SEQ ID NO: 4);

According to a preferred embodiment of the present invention, said polyclonal anti-BAG3 antibodies are obtained by immunizing the animals against one of the four peptides of the sequences SEQ ID NO: 1-4 stated above.

According to a preferred embodiment, the monoclonal anti-BAG3 antibodies of the present invention are obtained by means of a standard procedure (Tassone P., et al., Tissue Antigens 51: 671 (1998)) using the four MAP-BAG3 peptides described above and are produced by at least one of the nine mother clones chosen from the following: AC-1, AC-2, AC-3, AC-4, AC-5, AC-6, AC-7, AC-8, or AC-9 (described in WO03/055908), which contain specific hybridomas for each of the four MAP-BAG3 constructs used.

Said antibodies recognize the sequence of the four peptides of SEQ ID NO: 1-4.

According to a further embodiment, the antibodies used are monoclonal anti-BAG3 antibodies obtained from at least one of the aforesaid mother clones, and preferably at least one chosen from the following: AC-1, AC-2, AC-3, AC-4, or AC-5. More preferably, said monoclonal antibodies are obtained from at least one mother clone chosen from the following: AC-1, AC-2, and AC-3.

According to a further preferred embodiment, with the standard procedure (Ceran C, Cokol M, Cingoz S, Tasan I, Ozturk M, Yagci T. Novel anti-HER2 monoclonal antibodies: synergy and antagonism with tumor necrosis factor-α.BMC Cancer. 2012 Oct. 4; 12:450) and the immunization of mice with a BAG3 recombinant protein, the monoclonal anti-BAG3 antibodies envisaged in the present invention are obtained from at least one of the following clones: AC-rb1, AC-rb2, AC-rb3 and AC.rb4, and/or at least one of the following subclones: AC-rb1a, AC-rb1b, AC-rb2a, AC-rb2b, AC-rb3a, AC-rb3b, AC-rb4a, and AC-rb4b.

The monoclonal antibodies produced by all these clones and subclones recognize the BAG3 recombinant protein in an ELISA test.

Preferably, said monoclonal anti-BAG3 antibodies are those that recognize epitopes in the BAG3 protein amino acid sequence, which include at least one of the following fragments: 18-33, 385-399, 533-547 or 562-575.

More preferably said antibodies recognize the sequence of the four peptides of SEQ ID NOs: 1-4.

In a preferred embodiment of the present invention the humanized anti-BAG3 antibodies are the anti-BAG3 antibodies or fragments thereof disclosed in WO2017/076878.

Preferably the anti-BAG3 antibodies or fragments thereof usable according to the present invention are humanized antibodies which comprises:

a) a heavy chain amino acid sequence as encoded by SEQ ID NO: 12 or at least the variable domain thereof or an amino acid sequence having a sequence identity of at least 80% thereof, and b) a light chain amino acid sequence as encoded by SEQ ID NO: 20 or at least the variable domain thereof or an amino acid sequence having a sequence identity of at least 80% thereof.

As used herein, sequence identity between two polypeptide sequences, indicates the percentage of amino acids that are identical between the sequences, preferably over the entire length of the amino acid sequences as encoded by SEQ ID NO: 12 and SEQ ID NO: 20.

Preferred polypeptide sequences of the invention have a sequence identity of at least 85%, more preferably 90%, even more preferably 93%, 95%, 96%, 97%, 98% or 99%.

In a preferred embodiment of the present invention said amino acid sequence having a sequence identity of at least 80% with respect to SEQ ID NO: 12 is selected from SEQ ID NO: 14, SEQ ID N: 16 or SEQ ID NO: 18.

In a further preferred embodiment said amino acid sequence having a sequence identity of at least 80% with respect to SEQ ID NO: 20 is selected from SEQ ID NO: 22, SEQ ID N: 24 or SEQ ID NO: 26.

In a preferred embodiment the antibody of the present invention is the antibody wherein the heavy chain amino acid sequence is encoded by SEQ ID NO: 18 and the light chain amino acid sequence is encoded by SEQ ID NO 22 or SEQ ID NO: 26.

In a preferred embodiment, the heavy chain amino acid sequence or at least the variable domain thereof or an amino acid sequence having a sequence identity of at least 80% thereof, comprises the CDRs regions having the following amino acid composition: H-CDR1 comprises the amino acids GFNIKDTYMY (SEQ ID NO: 5), H-CDR2 comprises the amino acids GVDPANGNTRYDPKFQG (SEQ ID NO: 6), H-CDR3 comprises the amino acids DGAMDY (SEQ ID NO: 7) and the light chain amino acid sequence or at least the variable domain thereof or an amino acid sequence having a sequence identity of at least 80% thereof, comprises the CDRs regions having the following amino acid composition: L-CDR1 comprises the amino acids KSSQSLLYSSNQKNYLA (SEQ ID NO: 8), L-CDR2 comprises the amino acids WASTRES (SEQ ID NO: 9) and L-CDR3 comprises the amino acids QQYYTYPLT (SEQ ID NO: 10).

In a more preferred embodiment, the heavy chain amino acid sequence or at least the variable domain thereof or an amino acid sequence having a sequence identity of at least 90% thereof, comprises the CDRs regions having the following amino acid composition: H-CDR1 comprises the amino acids GFNIKDTYMY (SEQ ID NO: 5), H-CDR2 comprises the amino acids GVDPANGNTRYDPKFQG (SEQ ID NO: 6), H-CDR3 comprises the amino acids DGAMDY (SEQ ID NO: 7) and the light chain amino acid sequence or at least the variable domain thereof or an amino acid sequence having a sequence identity of at least 90% thereof, comprises the CDRs regions having the following amino acid composition: L-CDR1 comprises the amino acids KSSQSLLYSSNQKNYLA (SEQ ID NO: 8), L-CDR2 comprises the amino acids WASTRES (SEQ ID NO: 9) and L-CDR3 comprises the amino acids QQYYTYPLT (SEQ ID NO: 10).

In a further preferred embodiment, the heavy chain amino acid sequence or at least the variable domain thereof or an amino acid sequence having a sequence identity of at least 95% thereof, comprises the CDRs regions having the following amino acid composition: H-CDR1 comprises the amino acids GFNIKDTYMY (SEQ ID NO: 5), H-CDR2 comprises the amino acids GVDPANGNTRYDPKFQG (SEQ ID NO: 6), H-CDR3 comprises the amino acids DGAMDY (SEQ ID NO: 7) and the light chain amino acid sequence or at least the variable domain thereof or an amino acid sequence having a sequence identity of at least 95% thereof, comprises the CDRs regions having the following amino acid composition: L-CDR1 comprises the amino acids KSSQSLLYSSNQKNYLA (SEQ ID NO: 8), L-CDR2 comprises the amino acids WASTRES (SEQ ID NO: 9) and L-CDR3 comprises the amino acids QQYYTYPLT (SEQ ID NO: 10).

A further embodiment of the present invention, is an antibody or a fragment thereof which binds to the BAG3 protein and which comprises:

a) a heavy chain nucleotide sequence as encoded by SEQ ID NO: 11 or at least the variable domain thereof or a nucleotide sequence having a sequence identity of at least 80% thereof, and b) a light chain nucleotide sequence as encoded by SEQ ID NO: 19 or at least the variable domain thereof or a nucleotide sequence having a sequence identity of at least 80% thereof.

As used herein, "sequence identity" between two nucleotide sequences, indicates the percentage of nucleotides that are identical between the sequences, preferably over the entire length of the nucleotide sequences as encoded by SEQ ID NO: 11 and SEQ ID NO: 19.

Preferred nucleotide sequences of the invention have a sequence identity of at least 85%, more preferably 90%, even more preferably 93%, 95%, 96%, 97%, 98% or 99%.

In a preferred embodiment of the present invention said nucleotide sequence having a sequence identity of at least 80% with respect to SEQ ID NO: 11 is selected from SEQ ID NO: 13, SEQ ID N: 15 or SEQ ID NO: 17.

In a further preferred embodiment said amino acid sequence having a sequence identity of at least 80% with respect to SEQ ID NO: 19 is selected from SEQ ID NO: 21, SEQ ID NO: 23 or SEQ ID NO: 25.

In a preferred embodiment the antibody of the present invention is the antibody wherein the heavy chain amino acid sequence is encoded by SEQ ID NO: 17 and the light chain amino acid sequence is encoded by SEQ ID NO: 21 or SEQ ID NO: 25.

Monoclonal antibodies may be produced by any suitable method such as that of Köhler and Milstein (1975) or by recombinant DNA methods. Monoclonal antibodies may also be isolated from phage antibody libraries using techniques described in Clackson et al. (1991).

Humanized forms of the antibodies may be generated according to the methods known in the art, (Kettleborough C. A. et al., 1991), such as chimerization or CDR grafting. Alternative methods for the production of humanized antibodies are well known in the art and are described in, e.g., EP 0239400 and WO 90/07861. Human antibodies can also be derived by in vitro methods. Suitable examples include but are not limited to phage display, yeast display, and the like.

The humanized anti-BAG3 antibodies or fragments thereof according to the present invention are obtained according to the method disclosed in WO2017/076878. A further aim of the present invention is the use of the aforesaid anti-BAG3 antibodies in the treatment of a particular pathological state which involves the activation of macrophages and fibroblasts.

Such pathological states is a heart disease, wherein said heart disease is selected from angina pectoris, pre-infarction angina, myocardial infarction, heart failure, ischemia, acute coronary disease, acute heart failure, chronic heart failure and iatrogenic heart disease.

A further aim of the present invention is the use of a pharmaceutical composition comprising the aforesaid anti-BAG3 antibody in association with at least one pharmaceutically acceptable excipient in the treatment of cardiovascular diseases. Preferably, said cardiovascular diseases are selected from angina pectoris, pre-infarction angina, myocardial infarction, heart failure, ischemia, acute coronary disease, acute heart failure, chronic heart failure and iatrogenic heart disease.

The composition according to the present invention can be formulated in a form suitable for oral administration or in a form suitable for parenteral or topical administration.

In a preferred embodiment of the present invention, said oral form can be chosen from the following: tablets, capsules, solutions, suspensions, granules, and oily capsules.

In a further preferred embodiment of the present invention, said topical form can be chosen from the following: cream, ointment, ointment, solution, suspension, eye drops, pessary, nebuliser solution, spray, powder, or gel.

In a further preferred embodiment of this invention, said parenteral form can be either an aqueous buffer solution or an oily suspension.

Said parenteral administration include administration by intramuscular, intravenous, intradermal, subcutaneous, intraperitoneal, intranodal, or intrasplenic means.

EXAMPLE

Example 1

Myocardial infarct (MI) was induced using a model of cryoinfarction that produces a highly reproducible loss of myocardium. Briefly, 6 week-old mice (C75BL/6) were anesthetized by 2% isoflurane (v/v) oxygen mixture. The heart was exposed through a median sternotomy and the pericardium was opened. A 6-0 suture was placed at the apex of the LV (Left Ventricule). An 8 mm diameter cylindrical stamp was cooled in liquid nitrogen and then pressed on the LV free wall. Cryothermia was applied for 5 seconds.

Post-MI mice were randomized into two groups: the control group received intraperitoneal injection of control IgG1 (20 mg/Kg) while the experimental group received 20 mg/Kg of the murine anti-BAG3 mAb in PBS. Mice were treated 3 times a week for 5 weeks.

To measure global cardiac function, echocardiography was performed 5 weeks post-MI by use of the VisualSONICS VeVo 770 imaging system with a 710 scanhead in anesthetized animals (2% isoflurane, v/v). A) The internal diameter of the LV was measured in the short-axis view from M-mode recordings in end diastole and end systole. B) analysis software was used to calculate ejection fraction (EF) and fractional shortening (FS).

At the end of the experiment hearts were paraffin embedded. Sections (5 µm), mounted on glass slides, were processed and stained with Masson's trichrome staining kit (04-010802, Bio-Optica, Milano-Italy) according to the manufacture instructions. Images were acquired using a microscopy Olympus BX53 (2× objective).

As is showed in FIG. 1C, fibrosis increased in mice treated with PBS, while was markedly reduced in mice that received the murine anti-BAG3 mAb under the same conditions.

The obtained results demonstrated that in mice subjected to heart cryoinjury, LVEF was reduced after five weeks, but significantly higher in animals treated with a BAG-3 neutralizing monoclonal antibody (FIG. 1).

Therefore, the treatment with anti-BAG3 antibodies is able to reduce the inflammation and the fibrotic process in the cardiac tissue and to preserve the normal cardiac functions.

The invention claimed is:

1. A method for treating a cardiovascular disease in a patient, comprising the step of administering a pharmaceutical composition consisting essentially of an anti-BAG3 antibody to a patient in need thereof, where the cardiovascular disease is selected from the group consisting of: angina pectoris, pre-infarction angina, myocardial infarction, heart failure, ischemia, acute coronary disease, acute heart failure, chronic heart failure, and iatrogenic heart disease,
wherein the anti-BAG3 antibody is:
(i) a humanized antibody comprising a heavy chain comprising the amino acid sequence of SEQ ID NO: 12, 14, 16, or 18, and a light chain comprising the amino acid sequence of SEQ ID NO: 20, 22, 24, or 26; or
(ii) a humanized antibody comprising a heavy chain comprising H-CDR1 having the amino acid sequence of SEQ ID NO: 5, H-CDR2 having the amino acid sequence of SEQ ID NO: 6, and H-CDR3 having the amino acid sequence of SEQ ID NO: 7, and a light chain comprising L-CDR1 having the amino acid sequence of SEQ ID NO: 8, L-CDR2 having the amino acid sequence of SEQ ID NO: 9, and L-CDR3 having the amino acid sequence of SEQ ID NO: 10.

2. The method according to claim 1, wherein the anti-BAG3 antibody is a humanized antibody comprising the heavy chain comprising H-CDR1 having the amino acid sequence of SEQ ID NO: 5, H-CDR2 having the amino acid sequence of SEQ ID NO: 6, and H-CDR3 having the amino acid sequence of SEQ ID NO: 7, and the light chain comprising L-CDR1 having the amino acid sequence of SEQ ID NO: 8, L-CDR2 having the amino acid sequence of SEQ ID NO: 9, and L-CDR3 having the amino acid sequence of SEQ ID NO: 10.

3. The method according to claim 2, wherein the anti-BAG3 antibody is a humanized antibody comprising:
a) a heavy chain amino acid sequence comprising SEQ ID NO: 12 or an amino acid sequence having a sequence identity of at least 95% thereof, and
b) a light chain amino acid sequence comprising SEQ ID NO: 20 or an amino acid sequence having a sequence identity of at least 95% thereof.

4. The method according to claim 2, wherein the heavy chain of the humanized anti-BAG3 antibody comprises the amino acid sequence of SEQ ID NO: 14, SEQ ID NO: 16, or SEQ ID NO: 18.

5. The method according to claim 2, wherein the light chain of the humanized anti-BAG3 antibody comprises the amino acid sequence of SEQ ID NO: 22, SEQ ID NO: 24, or SEQ ID NO: 26.

6. The method according to claim 1, wherein the pharmaceutical composition is administered by oral administration, parenteral administration, or topical administration.

7. The method according to claim 6, wherein the pharmaceutical composition is orally administered in a form of tablets, capsules, solutions, suspensions, granules, or oily capsules.

8. The method according to claim 6, wherein the parenteral administration is intramuscular, intravenous, intradermal, subcutaneous, intraperitoneal, intranodal, or intrasplenic administration.

* * * * *

SEQUENCE LISTING

```
<160> NUMBER OF SEQ ID NOS: 26

<210> SEQ ID NO 1
<211> LENGTH: 16
<212> TYPE: PRT
<213> ORGANISM: Homo sapiens

<400> SEQUENCE: 1

Asp Arg Asp Pro Leu Pro Pro Gly Trp Glu Ile Lys Ile Asp Pro Gln
1               5                   10                  15
```

```
<210> SEQ ID NO 2
<211> LENGTH: 15
<212> TYPE: PRT
<213> ORGANISM: Homo sapiens

<400> SEQUENCE: 2

Ser Ser Pro Lys Ser Val Ala Thr Glu Glu Arg Ala Ala Pro Ser
1               5                   10                  15

<210> SEQ ID NO 3
<211> LENGTH: 15
<212> TYPE: PRT
<213> ORGANISM: Homo sapiens

<400> SEQUENCE: 3

Asp Lys Gly Lys Lys Asn Ala Gly Asn Ala Glu Asp Pro His Thr
1               5                   10                  15

<210> SEQ ID NO 4
<211> LENGTH: 15
<212> TYPE: PRT
<213> ORGANISM: Homo sapiens

<400> SEQUENCE: 4

Asn Pro Ser Ser Met Thr Asp Thr Pro Gly Asn Pro Ala Ala Pro
1               5                   10                  15

<210> SEQ ID NO 5
<211> LENGTH: 10
<212> TYPE: PRT
<213> ORGANISM: Homo sapiens

<400> SEQUENCE: 5

Gly Phe Asn Ile Lys Asp Thr Tyr Met Tyr
1               5                   10

<210> SEQ ID NO 6
<211> LENGTH: 17
<212> TYPE: PRT
<213> ORGANISM: Homo sapiens

<400> SEQUENCE: 6

Gly Val Asp Pro Ala Asn Gly Asn Thr Arg Tyr Asp Pro Lys Phe Gln
1               5                   10                  15
Gly

<210> SEQ ID NO 7
<211> LENGTH: 6
<212> TYPE: PRT
<213> ORGANISM: Homo sapiens

<400> SEQUENCE: 7

Asp Gly Ala Met Asp Tyr
1               5

<210> SEQ ID NO 8
<211> LENGTH: 17
<212> TYPE: PRT
<213> ORGANISM: Homo sapiens

<400> SEQUENCE: 8

Lys Ser Ser Gln Ser Leu Leu Tyr Ser Ser Asn Gln Lys Asn Tyr Leu
1               5                   10                  15
```

Ala

<210> SEQ ID NO 9
<211> LENGTH: 7
<212> TYPE: PRT
<213> ORGANISM: Homo sapiens

<400> SEQUENCE: 9

Trp Ala Ser Thr Arg Glu Ser
1               5

<210> SEQ ID NO 10
<211> LENGTH: 9
<212> TYPE: PRT
<213> ORGANISM: Homo sapiens

<400> SEQUENCE: 10

Gln Gln Tyr Tyr Thr Tyr Pro Leu Thr
1               5

<210> SEQ ID NO 11
<211> LENGTH: 1416
<212> TYPE: DNA
<213> ORGANISM: Homo sapiens
<220> FEATURE:
<221> NAME/KEY: source
<222> LOCATION: 1..1416
<223> OTHER INFORMATION: /mol_type="unassigned DNA"
      /organism="Homo sapiens"

<400> SEQUENCE: 11

| | |
|---|---|
| gcggccgcca tgaattttgg actgaggctg attttcctgg tgctgaccct gaaaggcgtc | 60 |
| cagtgtcagg tgcagctggt ccagagcggg gcagaggtga agaaaccagg tgccagcgtg | 120 |
| aaggtctctt gcaaagccag tggcttcaac atcaaggaca catacatgta ttgggtgcga | 180 |
| caggcccctg gccagggtct ggaatggatg gcggcgtgg accccgcaaa tggaaatact | 240 |
| agatacgatc ctaaatttca gggaaggggtg accatgacac gggacacttc aacctcgacg | 300 |
| gtctatatgg agctgtccag cctgagatcc gaagatacag ccgtgtacta ttgtgcccgc | 360 |
| gacggggcta tggattactg gggccaggga actctggtga ccgtctcgag cgctagcaca | 420 |
| aagggcccta gtgtgtttcc tctggctccc tcttccaaat ccacttctgg tggcactgct | 480 |
| gctctgggat gcctggtgaa ggattacttt cctgaacctg tgactgtctc atggaactct | 540 |
| ggtgctctga cttctggtgt ccacactttc cctgctgtgc tgcagtctag tggactgtac | 600 |
| tctctgtcat ctgtggtcac tgtgccctct tcatctctgg gaacccagac ctacatttgt | 660 |
| aatgtgaacc acaaaccatc caacactaaa gtggacaaaa agtggaaacc caaatcctgt | 720 |
| gacaaaaccc acacctgccc accttgtcct gcccctgaac tgctgggagg accttctgtg | 780 |
| tttctgttcc cccccaaacc aaaggatacc ctgatgatct ctagaacccc tgaggtgaca | 840 |
| tgtgtggtgg tggatgtgtc tcatgaggac cctgaggtca aattcaactg gtacgtggat | 900 |
| ggagtggaag tccacaatgc caaaaccaag cctagagagg aacagtacaa ttcaacctac | 960 |
| agagtggtca gtgtgctgac tgtgctgcat caggattggc tgaatggcaa ggaatacaag | 1020 |
| tgtaaagtct caaacaaggc cctgcctgct ccaattgaga aaacaatctc aaaggccaag | 1080 |
| ggacagccta gggaaccca gtctacacc ctgccacctt caagagagga aatgaccaaa | 1140 |
| aaccaggtgt ccctgacatg cctggtcaaa ggcttctacc cttctgacat tgctgtggag | 1200 |
| tgggagtcaa atggacagcc tgagaacaac tacaaaacaa ccccccctgt gctggattct | 1260 |

```
gatggctctt tctttctgta ctccaaactg actgtggaca agtctagatg gcagcagggg   1320
aatgtctttt cttgctctgt catgcatgag gctctgcata accactacac tcagaaatcc   1380
ctgtctctgt ctcccgggaa atgatagtaa aagctt                             1416
```

<210> SEQ ID NO 12
<211> LENGTH: 445
<212> TYPE: PRT
<213> ORGANISM: Homo sapiens

<400> SEQUENCE: 12

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Gly Val Asp Pro Ala Asn Gly Asn Thr Arg Tyr Asp Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Ala Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

```
Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 13
<211> LENGTH: 1416
<212> TYPE: DNA
<213> ORGANISM: Homo sapiens
<220> FEATURE:
<221> NAME/KEY: source
<222> LOCATION: 1..1416
<223> OTHER INFORMATION: /mol_type="unassigned DNA"
      /organism="Homo sapiens"

<400> SEQUENCE: 13
gcggccgcca tgaattttgg actgaggctg attttcctgg tgctgaccct gaaaggcgtc      60
cagtgtcagg tgcagctggt ccagtctgga gctgaggtga agaaaccagg agcctccgtg     120
aaggtctctt gcaaagccag tggcttcaac atcaaggaca catacatgta ttgggtgcga     180
caggcccctg gccagggtct ggaatggatg ggcggcgtgg accccgcaaa tggaaatact     240
agatacgatc taaatttca aggcagggtg accctgacac gggacacttc aacctcgacg     300
gtctatatgg agctgtccag cctgagatcc gaagatacag cagtgtacta ttgtgggcgc     360
gacggtgcta tggactactg gggccaggga actctggtga ccgtctcgag cgctagcaca     420
aagggcccta gtgtgtttcc tctggctccc tcttccaaat ccacttctgg tggcactgct     480
gctctgggat gcctggtgaa ggattacttt cctgaacctg tgactgtctc atggaactct     540
ggtgctctga cttctggtgt ccacactttc cctgctgtgc tgcagtctag tggactgtac     600
tctctgtcat ctgtggtcac tgtgccctct tcatctctgg aacccagac ctacatttgt     660 aatgtgaacc acaaaccatc caacactaaa gtggacaaaa agtggaaccc caaatcctgt     720
gacaaaaccc acacctgccc accttgtcct gcccctgaac tgctgggagg accttctgtg     780
tttctgttcc ccccaaaacc aaaggatacc ctgatgatct ctagaacccc tgaggtgaca     840
tgtgtggtgg tggatgtgtc tcatgaggac cctgaggtca aattcaactg gtacgtggat     900
ggagtggaag tccacaatgc caaaaccaag cctagagagg aacagtacaa ttcaacctac     960
agagtggtca gtgtgctgac tgtgctgcat caggattggc tgaatggcaa ggaatacaag    1020
tgtaaagtct caaacaaggc cctgcctgct ccaattgaga aacaatctc aaaggccaag    1080 ggacagccta gggaacccca ggtctacacc ctgccacctt caagagagga aatgaccaaa    1140
aaccaggtgt ccctgacatg cctggtcaaa ggcttctacc cttctgacat tgctgtggag    1200
tgggagtcaa atggacagcc tgagaacaac tacaaaacaa cccccctgt gctggattct    1260 gatggctctt ctttctgta ctccaaactg actgtggaca gtctagatg gcagcagggg    1320 aatgtctttt cttgctctgt catgcatgag gctctgcata accactacac tcagaaatcc    1380
ctgtctctgt ctcccgggaa atgatagtaa aagctt                             1416
```

```
<210> SEQ ID NO 14
<211> LENGTH: 445
<212> TYPE: PRT
<213> ORGANISM: Homo sapiens

<400> SEQUENCE: 14

Gln Val Gln Leu Val Gln Ser Gly Ala Glu Val Lys Pro Gly Ala
1               5                   10                  15

Ser Val Lys Val Ser Cys Lys Ala Ser Gly Phe Asn Ile Lys Asp Thr
            20                  25                  30

Tyr Met Tyr Trp Val Arg Gln Ala Pro Gly Gln Gly Leu Glu Trp Met
        35                  40                  45

Gly Gly Val Asp Pro Ala Asn Gly Asn Thr Arg Tyr Asp Pro Lys Phe
    50                  55                  60

Gln Gly Arg Val Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Gly Arg Asp Gly Ala Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
```

```
              370               375               380
Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 15
<211> LENGTH: 1416
<212> TYPE: DNA
<213> ORGANISM: Homo sapiens
<220> FEATURE:
<221> NAME/KEY: source
<222> LOCATION: 1..1416
<223> OTHER INFORMATION: /mol_type="unassigned DNA"
      /organism="Homo sapiens"

<400> SEQUENCE: 15
gcggccgcca tgaattttgg actgaggctg attttcctgg tgctgaccct gaaaggcgtc     60
cagtgtcagg tgcagctggt ccagtctgga gctgaggtga agaaaccagg agcctccgtg    120
aaggtctctt gcacagctag tggcttcaac atcaaggaca cttacatgta ttgggtgaaa    180
caggcccctg gccagggtct ggaatggatt ggcggcgtgg accccgcaaa cgggaatacc    240
agatacgatc taagtttca aggcaaagcc accctgacaa gggacacttc aacctcgacg    300
gtgtatatgg agctgtccag cctgaggtcc gaagatacag cagtgtacta ttgtgggcgg    360
gacggtgcta tggactactg gggccaggga actctggtga ccgtctcgag cgctagcaca    420
aagggcccta gtgtgtttcc tctggctccc tcttccaaat ccacttctgg tggcactgct    480
gctctgggat gcctggtgaa ggattacttt cctgaacctg tgactgtctc atggaactct    540
ggtgctctga cttctggtgt ccacactttc cctgctgtgc tgcagtctag tggactgtac    600
tctctgtcat ctgtggtcac tgtgccctct tcatctctgg aacccagac ctacatttgt    660 aatgtgaacc acaaccatc caacactaaa gtggacaaaa agtggaacc caaatcctgt    720 gacaaaaccc acacctgccc accttgtcct gcccctgaac tgctgggagg accttctgtg    780
tttctgttcc cccccaaacc aaaggatacc ctgatgatct ctagaaccc tgaggtgaca    840 tgtgtggtgg tggatgtgtc tcatgaggac cctgaggtca aattcaactg gtacgtggat    900
ggagtggaag tccacaatgc caaaaccaag cctagagagg aacagtacaa ttcaacctac    960
agagtggtca gtgtgctgac tgtgctgcat caggattggc tgaatggcaa ggaatacaag   1020
tgtaaagtct caaacaaggc cctgcctgct ccaattgaga aaacaatctc aaaggccaag   1080
ggacagccta gggaacccca ggtctacacc ctgccacctt caagagagga aatgaccaaa   1140
aaccaggtgt ccctgacatg cctggtcaaa ggcttctacc cttctgacat tgctgtggag   1200
tgggagtcaa atggacagcc tgagaacaac tacaaaacaa ccccccctgt gctggattct   1260
gatggctctt tctttctgta ctccaaactg actgtggaca gtctagatg gcagcagggg   1320 aatgtctttt cttgctctgt catgcatgag gctctgcata accactacac tcagaaatcc   1380
ctgtctctgt ctcccgggaa atgatagtaa aagctt                             1416

<210> SEQ ID NO 16
<211> LENGTH: 445
<212> TYPE: PRT
```

<213> ORGANISM: Homo sapiens

<400> SEQUENCE: 16

```
Gln Val Gln Leu Val Gln Ser Gly Ala Glu Val Lys Lys Pro Gly Ala
1               5                   10                  15

Ser Val Lys Val Ser Cys Thr Ala Ser Gly Phe Asn Ile Lys Asp Thr
            20                  25                  30

Tyr Met Tyr Trp Val Lys Gln Ala Pro Gly Gln Gly Leu Glu Trp Ile
        35                  40                  45

Gly Gly Val Asp Pro Ala Asn Gly Asn Thr Arg Tyr Asp Pro Lys Phe
    50                  55                  60

Gln Gly Lys Ala Thr Leu Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Gly Arg Asp Gly Ala Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 17
<211> LENGTH: 1416
<212> TYPE: DNA
<213> ORGANISM: Homo sapiens
<220> FEATURE:
<221> NAME/KEY: source
<222> LOCATION: 1..1416
<223> OTHER INFORMATION: /mol_type="unassigned DNA"
      /organism="Homo sapiens"

<400> SEQUENCE: 17
gcggccgcca tgaattttgg actgaggctg attttcctgg tgctgaccct gaaaggcgtc      60
cagtgtgagg tgcagctggt ccagagtggg gcagaagtga agaaaccagg tgccacagtg     120
aagatctcat gcaaagtctc cggcttcaac attaaggaca cttacatgta ttgggtgcag     180
caggcccccg gcaagggtct ggagtggatg gcggcgtgg accccgctaa cggcaatacc      240
agatacgatc taagtttca aggacgggtg accatcacag ctgacactag caccgatacg     300
gcatatatgg agctgtccag cctgagatct gaagatacag cagtgtacta ttgtgccagg     360
gacggggcta tggattactg gggccaggga actctggtga ccgtctcgag cgctagcaca     420
aagggcccta gtgtgtttcc tctggctccc tcttccaaat ccacttctgg tggcactgct     480
gctctgggat gcctggtgaa ggattacttt cctgaacctg tgactgtctc atggaactct     540
ggtgctctga cttctggtgt ccacactttc cctgctgtgc tgcagtctag tggactgtac     600
tctctgtcat ctgtggtcac tgtgccctct tcatctctgg aacccagac ctacatttgt      660 aatgtgaacc acaaaccatc caacactaaa gtggacaaaa agtggaacc caaatcctgt     720 gacaaaaccc acacctgccc accttgtcct gcccctgaac tgctgggagg accttctgtg     780
tttctgttcc ccccaaaacc aaaggatacc ctgatgatct ctagaacccc tgaggtgaca     840
tgtgtggtgg tggatgtgtc tcatgaggac cctgaggtca aattcaactg gtacgtggat     900
ggagtggaag tccacaatgc caaaaccaag cctagagagg aacagtacaa ttcaacctac     960
agagtggtca gtgtgctgac tgtgctgcat caggattggc tgaatggcaa ggaatacaag    1020
tgtaaagtct caaacaaggc cctgcctgct ccaattgaga aaacaatctc aaaggccaag    1080
ggacagccta gggaacccca ggtctacacc ctgccaccct caagagagga aatgaccaaa    1140
aaccaggtgt ccctgacatg cctggtcaaa ggcttctacc cttctgacat tgctgtggag    1200
tgggagtcaa atggacagcc tgagaacaac tacaaaacaa cccccccctgt gctggattct    1260 gatggctctt tctttctgta ctccaaactg actgtggaca gtctagatg gcagcagggg    1320 aatgtctttt cttgctctgt catgcatgag gctctgcata accactacac tcagaaatcc    1380
ctgtctctgt ctcccgggaa atgatagtaa aagctt                               1416

<210> SEQ ID NO 18
<211> LENGTH: 445
<212> TYPE: PRT
<213> ORGANISM: Homo sapiens

<400> SEQUENCE: 18

Glu Val Gln Leu Val Gln Ser Gly Ala Glu Val Lys Lys Pro Gly Ala

-continued

```
1               5                   10                  15
Thr Val Lys Ile Ser Cys Lys Val Ser Gly Phe Asn Ile Lys Asp Thr
                20                  25                  30
Tyr Met Tyr Trp Val Gln Gln Ala Pro Gly Lys Gly Leu Glu Trp Met
            35                  40                  45
Gly Gly Val Asp Pro Ala Asn Gly Asn Thr Arg Tyr Asp Pro Lys Phe
        50                  55                  60
Gln Gly Arg Val Thr Ile Thr Ala Asp Thr Ser Thr Asp Thr Ala Tyr
 65                 70                  75                  80
Met Glu Leu Ser Ser Leu Arg Ser Glu Asp Thr Ala Val Tyr Tyr Cys
                85                  90                  95
Ala Arg Asp Gly Ala Met Asp Tyr Trp Gly Gln Gly Thr Leu Val Thr
            100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
            130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
            275                 280                 285
Pro Arg Glu Glu Gln Tyr Asn Ser Thr Tyr Arg Val Val Ser Val Leu
            290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
```

His Tyr Thr Gln Lys Ser Leu Ser Leu Ser Pro Gly Lys
        435                 440                 445

<210> SEQ ID NO 19
<211> LENGTH: 741
<212> TYPE: DNA
<213> ORGANISM: Homo sapiens
<220> FEATURE:
<221> NAME/KEY: source
<222> LOCATION: 1..741
<223> OTHER INFORMATION: /mol_type="unassigned DNA"
      /organism="Homo sapiens"

<400> SEQUENCE: 19

```
gcggccgcca tgaattttgg actgaggctg attttcctgg tgctgaccct gaaaggcgtc      60
cagtgtgaca tcgtgatgac acagtcacct gattccctgg cagtcagtct gggcgagaga     120
gccactatta actgcaagtc cagccagtct ctgctgtact ctagtaacca gaaaaattac     180
ctggcttggt atcagcagaa gccagggcag cccctaaac tgctgatcta ttgggcaagc      240
accagggaat ctggagtgcc cgaccggttc agcggttctg gcagtggaac agattttacc     300
ctgacaattt catccctgca agccgaggac gtggctgtct actattgtca gcagtactat     360
acttacccac tgaccttcgg cggagggacc aagctcgaga tcaaacgtac ggtcgcggcg     420
ccttctgtgt tcattttccc cccatctgat gaacagctga atctggcac tgcttctgtg      480
gtctgtctgc tgaacaactt ctaccctaga gaggccaaag tccagtggaa agtggacaat     540
gctctgcaga gtgggaattc ccaggaatct gtcactgagc aggactctaa ggatagcaca     600
tactccctgt cctctactct gacactgagc aaggctgatt acgagaaaca caaagtgtac     660
gcctgtgaag tcacacatca ggggctgtct agtcctgtga ccaaatcctt caataggga      720
gagtgctgat agtaaaagct t                                               741
```

<210> SEQ ID NO 20
<211> LENGTH: 220
<212> TYPE: PRT
<213> ORGANISM: Homo sapiens

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu

```
                145                 150                 155                 160
        Gln Ser Gly Asn Ser Gln Glu Ser Val Thr Glu Gln Asp Ser Lys Asp
                        165                 170                 175

Ser Thr Tyr Ser Leu Ser Ser Thr Leu Thr Leu Ser Lys Ala Asp Tyr
                        180                 185                 190

Glu Lys His Lys Val Tyr Ala Cys Glu Val Thr His Gln Gly Leu Ser
                        195                 200                 205

Ser Pro Val Thr Lys Ser Phe Asn Arg Gly Glu Cys
                        210                 215                 220

<210> SEQ ID NO 21
<211> LENGTH: 741
<212> TYPE: DNA
<213> ORGANISM: Homo sapiens
<220> FEATURE:
<221> NAME/KEY: source
<222> LOCATION: 1..741
<223> OTHER INFORMATION: /mol_type="unassigned DNA"
      /organism="Homo sapiens"

<400> SEQUENCE: 21
gcggccgcca tgaattttgg actgaggctg attttcctgg tgctgaccct gaaaggcgtc      60
cagtgtgaca tcgtgatgac acagtcacct gattccctgg cagtcagtct gggcgagaga     120
gccactatta actgcaagtc cagccagtct ctgctgtact ctagtaacca gaaaaattat     180
ctggcttggc accagcagaa gccagggcag ccccctaaac tgctgatcta ctgggcaagc     240
accagggaat ctggagtgcc cgaccggttc agcggttctg gcagtggaac agattttacc     300
ctgacaattt catccctgca agccgaggac gtggctgtct actattgtca gcagtactat     360
acttatccac tgaccttcgg cggagggacc aagctcgaga tcaaacgtac ggtcgcggcg     420
ccttctgtgt tcatttttcc cccatctgat gaacagctga atctggcac tgcttctgtg     480 gtctgtctgc tgaacaactt ctaccctaga gaggccaaag tccagtggaa agtggacaat     540
gctctgcaga gtgggaattc caggaatct gtcactgagc aggactctaa ggatagcaca     600 tactcccctgt cctctactct gacactgagc aaggctgatt acgagaaaca caaagtgtac     660
gcctgtgaag tcacacatca ggggctgtct agtcctgtga ccaaatcctt caataggga     720 gagtgctgat agtaaaagct t                                                741

<210> SEQ ID NO 22
<211> LENGTH: 220
<212> TYPE: PRT
<213> ORGANISM: Homo sapiens

<400> SEQUENCE: 22

Asp Ile Val Met Thr Gln Ser Pro Asp Ser Leu Ala Val Ser Leu Gly
        1               5                  10                  15

Glu Arg Ala Thr Ile Asn Cys Lys Ser Ser Gln Ser Leu Leu Tyr Ser
                        20                 25                  30

Ser Asn Gln Lys Asn Tyr Leu Ala Trp His Gln Gln Lys Pro Gly Gln
                        35                 40                  45

Pro Pro Lys Leu Leu Ile Tyr Trp Ala Ser Thr Arg Glu Ser Gly Val
                50                 55                  60

Pro Asp Arg Phe Ser Gly Ser Gly Ser Gly Thr Asp Phe Thr Leu Thr
        65                     70                  75                  80

Ile Ser Ser Leu Gln Ala Glu Asp Val Ala Val Tyr Tyr Cys Gln Gln
                        85                 90                  95
```

Tyr Tyr Thr Tyr Pro Leu Thr Phe Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 23
<211> LENGTH: 741
<212> TYPE: DNA
<213> ORGANISM: Homo sapiens
<220> FEATURE:
<221> NAME/KEY: source
<222> LOCATION: 1..741
<223> OTHER INFORMATION: /mol_type="unassigned DNA"
      /organism="Homo sapiens"

<400> SEQUENCE: 23
gcggccgcca tgaattttgg actgaggctg attttcctgg tgctgaccct gaaaggcgtc      60
cagtgtgaca tcgtgatgac acagtcacct gattccctgg cagtctccct gggcgagaga     120
gccactatga gttgcaagtc cagccagtct ctgctgtact ctagtaacca gaaaaattat     180
ctggcttggc accagcagaa gccagggcag cccctaaac tgctgatcta ctgggcaagc      240
accagggaat ctggagtgcc cgaccggttc agcggttctg gcagtggaac agattttacc     300
ctgacaattt catccctgca agccgaggac gtggctgtct actattgtca gcagtactat     360
acttatccac tgaccttcgg cggagggacc aagctcgaga tcaagcgtac ggtcgcggcg     420
ccttctgtgt tcattttccc cccatctgat gaacagctga atctggcac tgcttctgtg      480
gtctgtctgc tgaacaactt ctaccctaga gaggccaaag tccagtggaa agtggacaat     540
gctctgcaga gtgggaattc caggaatct gtcactgagc aggactctaa ggatagcaca      600
tactccctgt cctctactct gacactgagc aaggctgatt acgagaaaca caaagtgtac     660
gcctgtgaag tcacacatca ggggctgtct agtcctgtga ccaaatcctt caatagggga     720
gagtgctgat agtaaaagct t                                              741

<210> SEQ ID NO 24
<211> LENGTH: 220
<212> TYPE: PRT
<213> ORGANISM: Homo sapiens

<400> SEQUENCE: 24

Asp Ile Val Met Thr Gln Ser Pro Asp Ser Leu Ala Val Ser Leu Gly
1               5                   10                  15

Glu Arg Ala Thr Met Ser Cys Lys Ser Ser Gln Ser Leu Leu Tyr Ser
            20                  25                  30

Ser Asn Gln Lys Asn Tyr Leu Ala Trp His Gln Gln Lys Pro Gly Gln
        35                  40                  45

-continued

```
Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 25
<211> LENGTH: 741
<212> TYPE: DNA
<213> ORGANISM: Homo sapiens
<220> FEATURE:
<221> NAME/KEY: source
<222> LOCATION: 1..741
<223> OTHER INFORMATION: /mol_type="unassigned DNA"
      /organism="Homo sapiens"

<400> SEQUENCE: 25

```
gcggccgcca tgaattttgg actgaggctg attttcctgg tgctgaccct gaaaggcgtc    60
cagtgtgaca tcgtgatgac acagtcacct gattccctgg cagtctccct gggcgagaga   120
gccactatga gttgcaagtc cagccagtct ctgctgtact ctagtaacca gaaaaattat   180
ctggcttggc accagcagaa gccaggacag ccccctaaac tgctgatcta ctgggcaagc   240
acccgggaat ctggcgtgcc cgaccggttc agcggctctg gaagtgggac agattttacc   300
ctgacaatct catccctgca agccgaggac ctggctatct actattgtca gcagtactat   360
acttatccac tgaccttcgg tgccggcacc aagctcgaga tcaaacgtac ggtcgcggcg   420
ccttctgtgt tcatttttccc cccatctgat gaacagctga atctggcac tgcttctgtg   480
gtctgtctgc tgaacaactt ctaccctaga gaggccaaag tccagtggaa agtggacaat   540
gctctgcaga gtgggaattc caggaatct gtcactgagc aggactctaa ggatagcaca   600
tactccctgt cctctactct gacactgagc aaggctgatt acgagaaaca caaagtgtac   660
gcctgtgaag tcacacatca ggggctgtct agtcctgtga ccaaatcctt caatagggga   720
gagtgctgat agtaaaagct t                                             741
```

<210> SEQ ID NO 26
<211> LENGTH: 220
<212> TYPE: PRT
<213> ORGANISM: Homo sapiens

```
<400> SEQUENCE: 26

Asp Ile Val Met Thr Gln Ser Pro Asp Ser Leu Ala Val Ser Leu Gly
1               5                   10                  15

Glu Arg Ala Thr Met Ser Cys Lys Ser Ser Gln Ser Leu Leu Tyr Ser
            20                  25                  30

Ser Asn Gln Lys Asn Tyr Leu Ala Trp His Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Leu Ala Ile Tyr Tyr Cys Gln Gln
                85                  90                  95

Tyr Tyr Thr Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
210                 215                 220
```